(12) United States Patent
Burri et al.

(10) Patent No.: US 6,521,183 B1
(45) Date of Patent: Feb. 18, 2003

(54) AUTOMATIC ANALYZER SYSTEM

(75) Inventors: Martin Burri, Bettwil (CH); Leo Schwerzmann, Udligenswil (CH)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/569,952

(22) Filed: May 12, 2000

(30) Foreign Application Priority Data

May 14, 1999 (EP) .............................................. 99810433

(51) Int. Cl.$^7$ .......................... G01N 21/00; G01N 35/04
(52) U.S. Cl. .............................. 422/65; 436/43; 436/46; 436/47; 436/48
(58) Field of Search ................................ 422/65, 99, 63, 422/67, 68.1; 436/43, 45, 72; 198/347.3, 348

(56) References Cited

U.S. PATENT DOCUMENTS 5,207,986 A    5/1993   Kodata et al.

FOREIGN PATENT DOCUMENTS

| DE | 19742160 | 9/1997 |
|----|----------|--------|
| EP | 856736 A2 | 8/1998 |
| JP | 63218035 | 3/1990 |

*Primary Examiner*—Jill Warden
*Assistant Examiner*—Sam P. Siefke

(74) *Attorney, Agent, or Firm*—Gibbons, Del Deo, Dolan, Griffinger & Vecchione (57) ABSTRACT

An automatic analyzer system including transport means for moving sample racks within the system. In order to simplify and reduce the cost of the means for transporting the sample racks the system comprises (a) a rack supply unit capable of containing sample racks, said rack supply unit including (a.1) a rack input device for introducing sample racks into the rack supply unit, (a.2) a rack output device for removing sample racks from the rack supply unit, (a.3) a buffer unit for storing unprocessed racks before they are transferred from said rack supply unit to a position corresponding to an analyzer unit, and for storing also already processed racks which contain samples having a probability of being reexamined, and (a.4) means for moving a sample rack from said rack input device and from said rack output device to said buffer unit and vice versa; (b) at least one analyzer unit for testing an analysis item of a sample sampled from a sample container (91) contained in a sample rack, said buffer unit being so arranged as to be interposed between said rack input/output devices (13, 14) and said at least one analyzer unit (21, 31); (c) a single transfer line for moving a sample rack from said buffer unit to a position corresponding to said at least one analyzer unit and for moving said sample rack from said position back to said buffer unit; (d) means for moving said sample rack in opposite senses along said single transfer line, and (e) means for directing a sample rack from said rack input device and said rack output device to said buffer unit and vice versa; and (f) means for directing a sample rack from said buffer unit to said at least one analyzer unit and vice versa.

12 Claims, 7 Drawing Sheets

AUTOMATIC ANALYZER SYSTEM

FIELD OF INVENTION

The invention concerns an automatic analyzer system including a rack supply unit capable of containing sample racks, an analyzer unit for testing an analysis item of a sample sampled from a sample container contained in a sample rack, and a transfer line for moving a sample rack from the buffer unit to a position corresponding to the analyzer unit.

BACKGROUND OF THE INVENTION

A system of the above mentioned kind is described in European Patent Application EP-A-0856736 A2. This known system comprises two separate transfer lines: a first transfer line for bringing a sample rack from a rack supply unit to an analyzer unit, and a second transfer line for bringing racks containing samples to be re-examined from the output end of the first transfer line back to the input end of the a first transfer line. In addition to the rack supply unit, this known system comprises a stand-by unit for temporarily storing racks containing samples having a probability of being re-examined, a collecting unit for storing racks containing samples which do not have to be re-examined and which should leave the system, first mechanical means for transferring a sample rack from the rack supply unit to the input end of the first transfer line, second mechanical means for transferring a sample rack from the output end of the first transfer line to the input of the stand-by unit, third mechanical means for transferring a sample rack from the output end of the stand-by unit either to the input end of the second transfer line or to the input end of the collecting unit. The stand-by unit is located close to the output end of the first transfer line, and the collecting unit is adjacent to the stand-by unit. As can be appreciated from the above description of the prior art system described in EP-A-0856736 A2, such a system is rather complex and therefore relatively expensive.

The aim of the invention is therefore to provide a system of the above mentioned kind which has a more simple structure and which is therefore less expensive, and which makes it possible however transport a sufficient number of samples per time unit within such a system.

SUMMARY OF THE INVENTION

According to the invention, this aim is achieved with an automatic analyzer system comprising (a) a rack supply unit capable of containing sample racks, the rack supply unit including
  (a.1) a rack input device for introducing sample racks into the rack supply unit,
  (a.2) a rack output device for removing sample racks from the rack supply unit,
  (a.3) a buffer unit for storing unprocessed racks before they are transferred from the rack supply unit to a position corresponding to an analyzer unit, and for storing also already processed racks which contain samples having a probability of being reexamined, and
  (a.4) means for moving racks from the rack input device and the rack output device to the buffer unit and vice versa;
(b) at least one analyzer unit for testing an analysis item of a sample sampled from a sample container contained in a sample rack, the buffer unit being so arranged as, to be interposed between the input/output unit and the at least one analyzer unit, (c) a single transfer line for moving a sample rack from the buffer unit to a position corresponding to the at least one analyzer unit and for moving the sample rack from the position back to the buffer unit, (d) means for moving the sample rack in opposite senses along said single transfer line, and (e) means for directing a sample rack from the rack input device and the rack output device to the buffer unit or vice versa, and (f) means for directing a sample rack from the buffer unit to the at least one analyzer unit or vice versa.

The main advantages of a system according to the invention over the above mentioned prior art are a much simpler structure of the means for transporting sample racks and therefore a corresponding reduction of the cost of such means.

BRIEF DESCRIPTION OF THE DRAWINGS

Preferred embodiments of the invention are described hereinafter more in detail with reference to the accompanying drawings.

DETAILED DESCRIPTION OF THE INVENTION

FIRST EMBODIMENT

Figure 1:
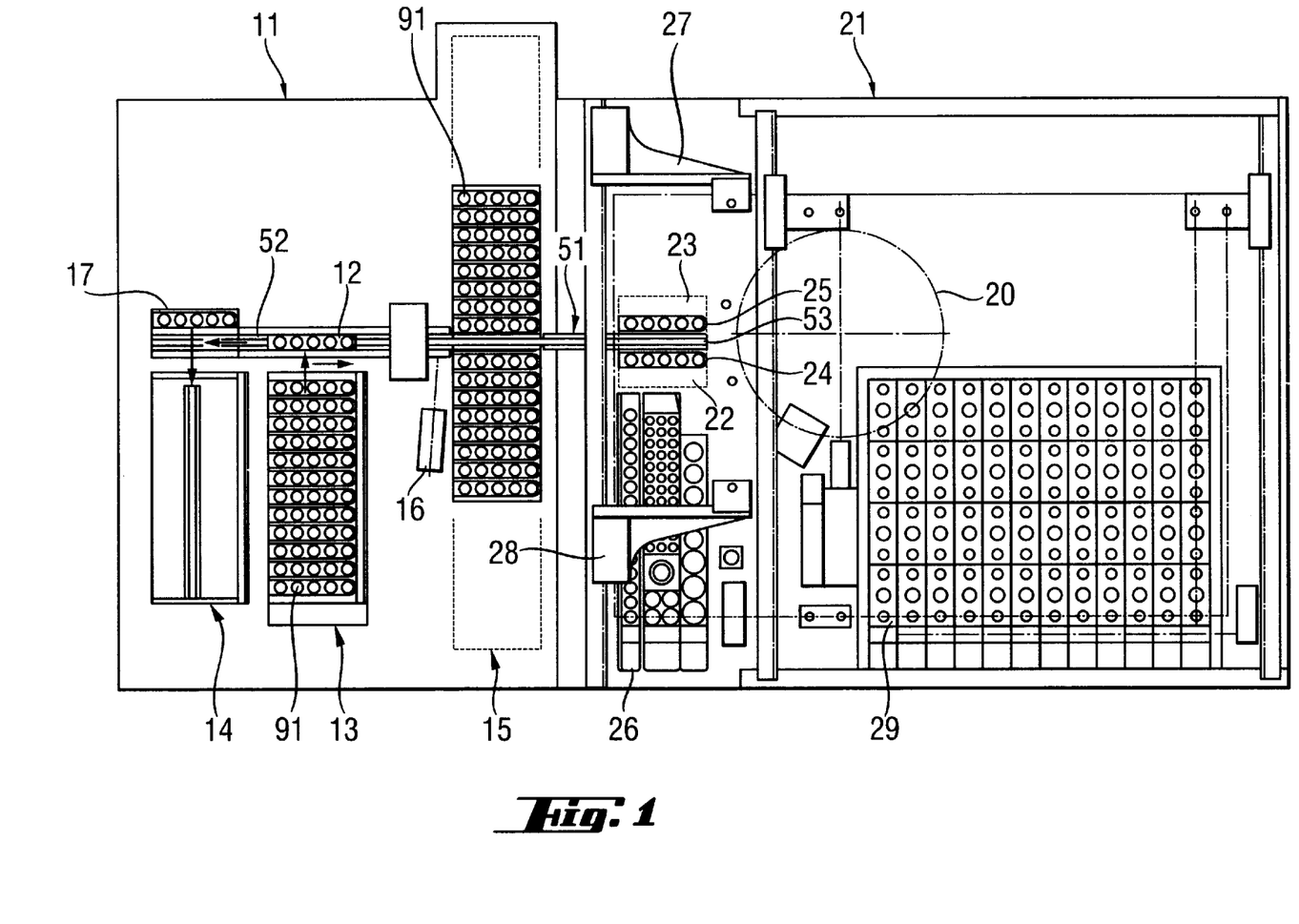
FIG. 1 shows a top view of a first embodiment of an analyzer system according to the invention.
Figure 2:
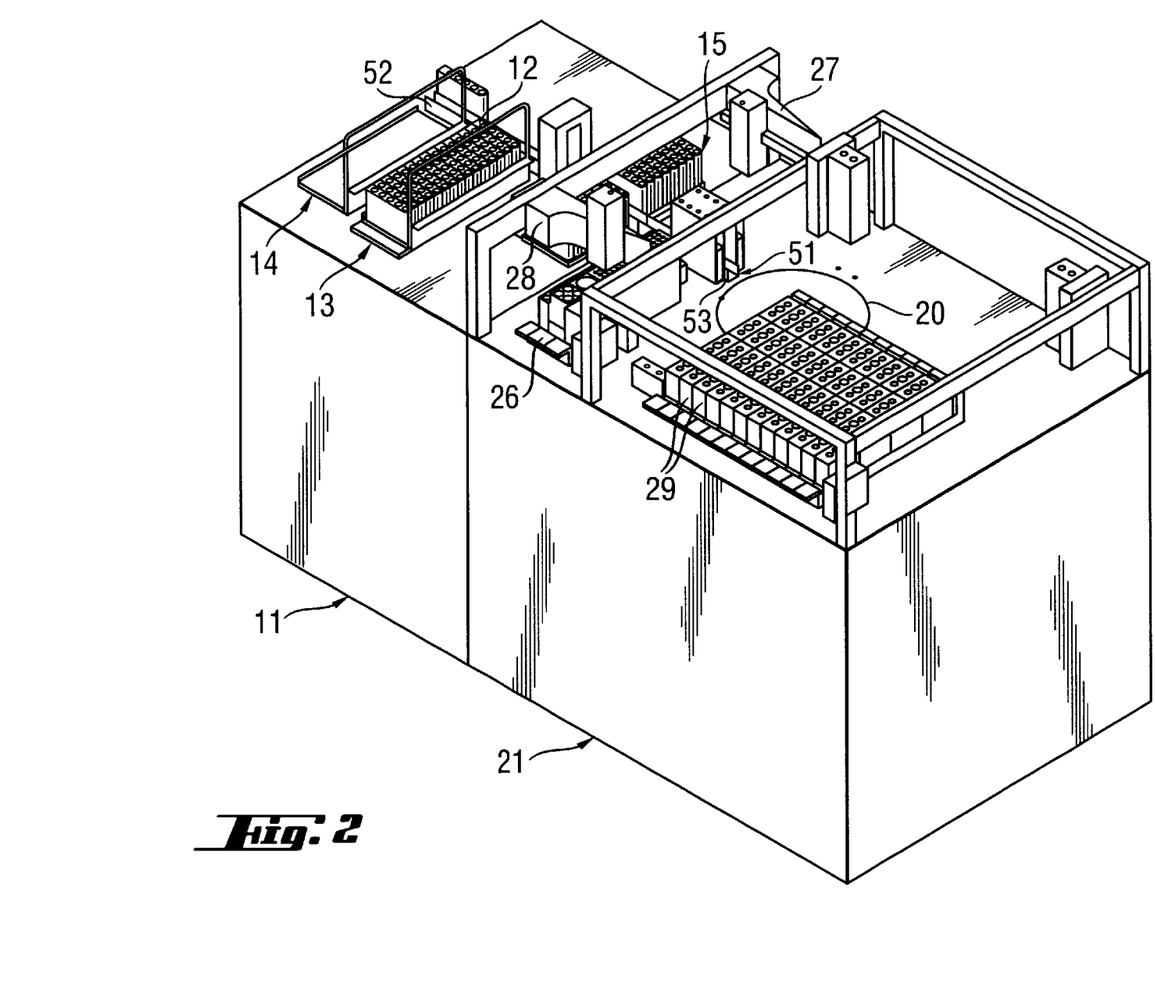
FIG. 2 shows a schematic perspective view of the embodiment shown by FIG. 1.

As shown by FIGS. 1 and 2, a first embodiment of an analyzer system according to the invention comprises a rack supply unit 11 and at least one analyzer unit 21 for testing an analysis item of a biological sample sampled from a sample container 91 contained in a sample rack 12.

Rack supply unit 11 comprises a rack input device 13 for introducing sample racks 12 into the rack supply unit 11, a rack output device 14 for removing sample racks 12 from the rack supply unit 11, a buffer unit 15 for storing unprocessed racks before they are transferred from said rack supply unit 11 to a position 22 or 23 corresponding to analyzer unit 21, and for storing also already processed racks which contain samples having a probability of being reexamined, and means for moving a sample rack 12 from rack input device 13 and from rack output device 14 to buffer unit 15 and vice versa.

Rack supply unit 11 also comprises an scanner 16 for reading bar code identification of each sample rack 12 and of each sample container 91 contained in a sample rack as it is moved from rack input device 13 to buffer unit 15.

Rack input device 13 and rack output device 14 are arranged side-by-side and form together a rack input/output device 13,14. Buffer unit 15 is so arranged as to be interposed between such a rack input/output device 13, 14 and the analyzer unit 21.

In a preferred embodiment, a system according to the invention offers the possibility of manually introducing a sample rack which needs urgent processing (a rack containing so called STAT-samples, short designation of "short turn around time"-samples), like rack 17 in FIG. 1, directly to single transfer line 51.

A system according to the invention has a single transfer line 51 for moving a sample rack 12 from buffer unit 15 to one of two parking positions 22 or 23 corresponding to, and preferably located on, analyzer unit 21 and for moving said sample rack 12 from parking position 22 or 23 back to buffer unit 15. For this purpose a system according to the invention comprises means for moving a sample rack 12 in opposite senses along single transfer line 51. In a preferred embodiment a part of single transfer line 51 is also used for moving a sample rack 12 from rack input device 13 and rack output device 14 to buffer unit 15 and vice versa.

In a preferred embodiment only two stationary parking positions or areas 22, 23 are provided for analyzer unit 21, and each of these parking positions or areas is apt to receive only one sample rack 24, 25 at a time.

One of parking positions 22, 23 is used for receiving a sample rack 24 with respect to which analyzer unit 21 is enabled to carry out pipetting operations, whereas the other parking position 23 is used as stand-by position for another sample rack 25, and each of the two parking positions 22, 23 is apt to be used as stand-by position for a sample rack while pipetting operations are effected on sample tubes contained in another sample rack positioned at the other parking position.

A system according to the invention also comprises means for directing a sample rack 12 from rack input device 13 and rack output device 14 to buffer unit 15 and vice versa, and means for directing a sample rack 12 from buffer unit 15 to one of the parking positions 22, 23 of analyzer unit 21 and vice versa. Such means for directing a sample rack 12 from one position to another include a central data processing and control unit (not shown in FIGS. 1 and 2, but shown in FIG. 5 as unit 61) which provides an overall control at the system level and cooperates with the local control system of analyzer unit 21.

In a preferred embodiment, single transfer line 51 is built by assembling at least two separate transfer line portions 52, 53. In the example shown by FIG. 1 transfer line portion 52 is part of rack supply unit 11 and transfer line portion 53 is part of analyzer unit 21.

In a preferred embodiment the alignment of rack supply unit 11 with analyzer unit 21 shown by FIGS. 1 and 2 is ensured by suitable means, like e.g. positioning pins or equivalent means.

Operation of the system shown by FIG. 1 is as follows:

Groups of sample racks 12 are introduced into rack input device 13 which is for instance a tray. Suitable mechanical means transfer sample racks one-by-one from rack input device 13 to part 52 of transfer line 51 which moves the sample rack and brings it into buffer unit 15. In buffer 15 the sample racks are displaced laterally in opposite senses so as to leave the central position of buffer unit 15 free for sample racks arriving to buffer unit 15 either from the side of rack input device 13 or from the side of analyzer unit 21.

Sample racks which are brought by single transfer line 51 from buffer unit 15 to any of the parking positions 22, 23 are first moved along transfer line 51 until they reach a position close to one of said parking positions 22, 23 and then suitable mechanical means move the sample rack from that position to one of said parking positions 22, 23, so that the transfer line 51 becomes free for transporting another sample rack.

Once a sample rack e.g. 24 has reached parking position 22 the system control enables pipetting unit 27 or 28 of analyzer unit 21 to perform pipetting operations on samples contained in sample rack 24. If during these operations a second sample rack 25 arrives to analyzer 21, such a sample rack 25 is brought by said suitable mechanical means to stand-by parking position 23.

Sample portions taken from sample containers in a sample rack like rack 24 are pipetted into reaction tubes located in a rotatable analyzer device 20 which forms part of analyzer unit 21. The necessary reagents are automatically and selectively sampled from reagent containers 29 and pipetted into said reaction tubes in order to form sample-reagent-mixtures. These mixtures are then analyzed in analyzer device 20.

When processing of a sample rack in one of the parking positions 22, 23 is terminated the control means of the system direct the sample rack back to buffer unit 15 by moving first the sample rack from the parking position to the transfer line 51 and then via transfer line to buffer unit 15.

SECOND EMBODIMENT

Figure 3:
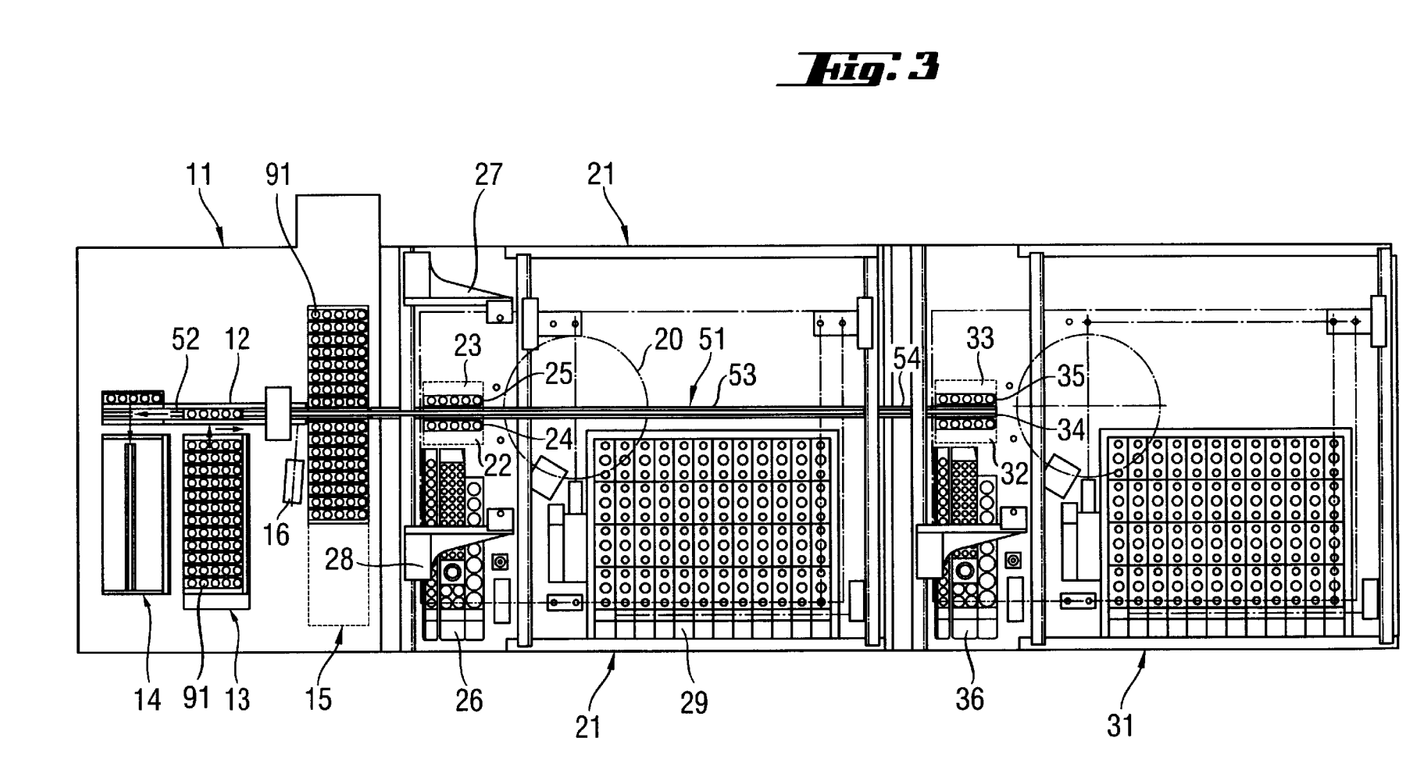
FIG. 3 shows a top view of a second embodiment of an analyzer system according to the invention.
Figure 4:
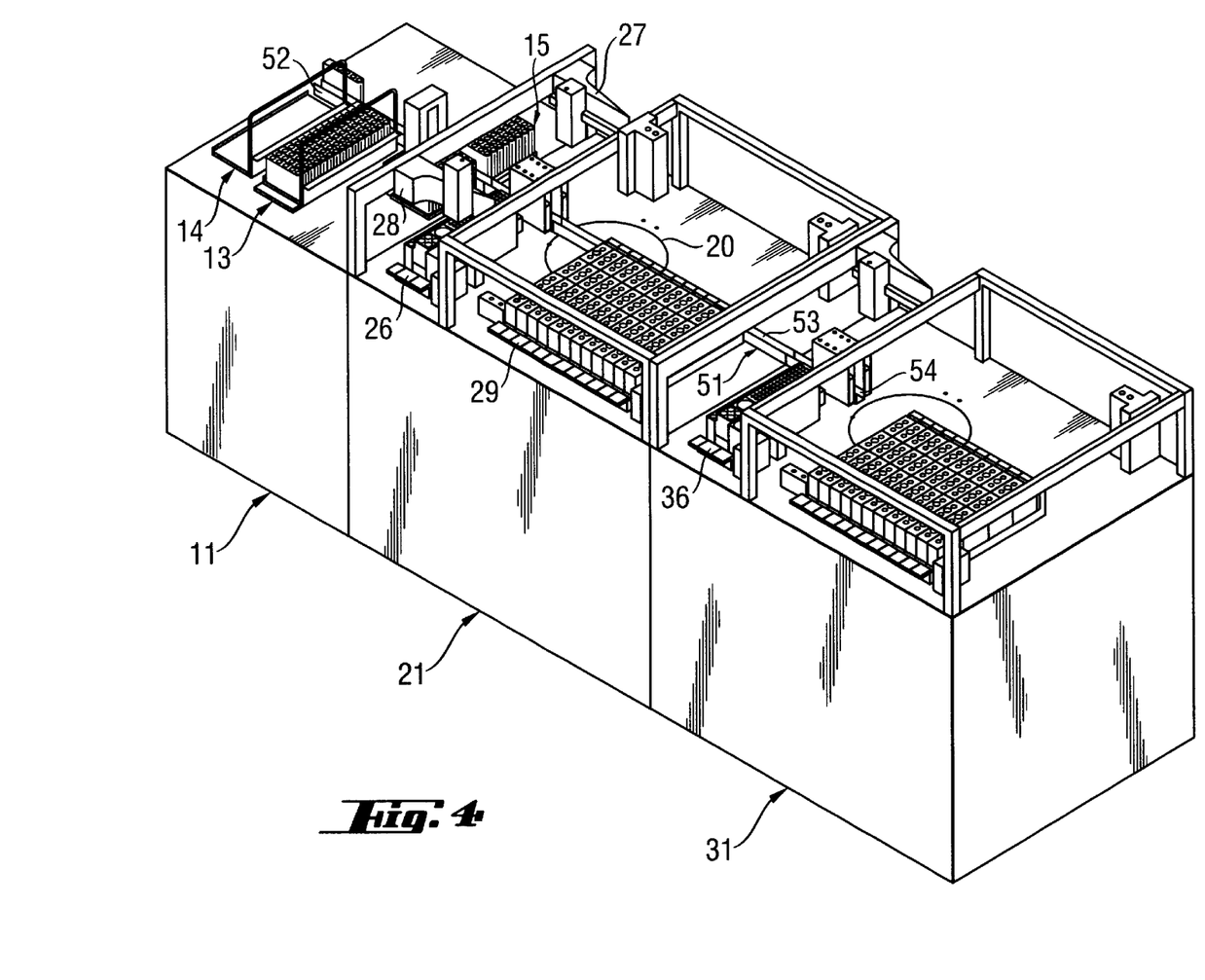
FIG. 4 shows a schematic perspective view of the embodiment shown by FIG. 3.

As shown by FIGS. 3 and 4, a second embodiment of an analyzer system according to the invention has basically the same structure as the first embodiment shown by FIGS. 1 and 2, but differs therefrom in that it comprises an additional analyzer unit 31.

In this second embodiment, a part 54 of single transfer line 51 extends over analyzer unit 31 and single transfer line 51 is in addition used for moving a sample rack 12 from buffer unit 15 to one of two parking positions 32 or 33 corresponding to, and preferably located on, analyzer unit 31 and for moving said sample rack 12 from parking position 32 or 33 back to buffer unit 15.

In a preferred embodiment only two stationary parking positions or areas 32, 33 are provided for analyzer unit 31, and each of these parking positions or areas is apt to receive only one sample rack 34, 35 at a time.

One of parking positions 32, 33 is used for receiving a sample rack 34 with respect to which analyzer unit 31 is enabled to carry out pipetting operations, whereas the other parking position 33 is used as stand-by position for another sample rack 35, and each of the two parking positions 32, 33 is apt to be used as stand-by position for a sample rack while pipetting operations are effected on sample container as contained in another sample rack positioned at the other parking position.

In a preferred embodiment, single transfer line 51 is built by assembling separate transfer line portions 52, 53, 54. In the example shown by FIG. 3 transfer line portion 52 is part of rack supply unit 11, transfer line portion 53 is part of analyzer unit 21, and transfer line portion 54 is part of analyzer unit 31.

The system shown by FIGS. 3 and 4 comprises means for directing a sample rack 12 from buffer unit 15 to one of the two parking positions 32, 33 of analyzer unit 21 and vice versa. Such means for directing a sample rack 12 from one position to another include a central data processing and control unit (not shown in FIGS. 3 and 4, but shown in FIG. 5 as unit 61) which provides an overall control at the system level and cooperates with the local control system of analyzer unit 31.

In a preferred embodiment the alignment of rack supply unit 11 with analyzer units 21 and 31 shown by FIGS. 3 and 4 is ensured by suitable means, like e.g. positioning pins or equivalent means.

THIRD EMBODIMENT

Figure 5:
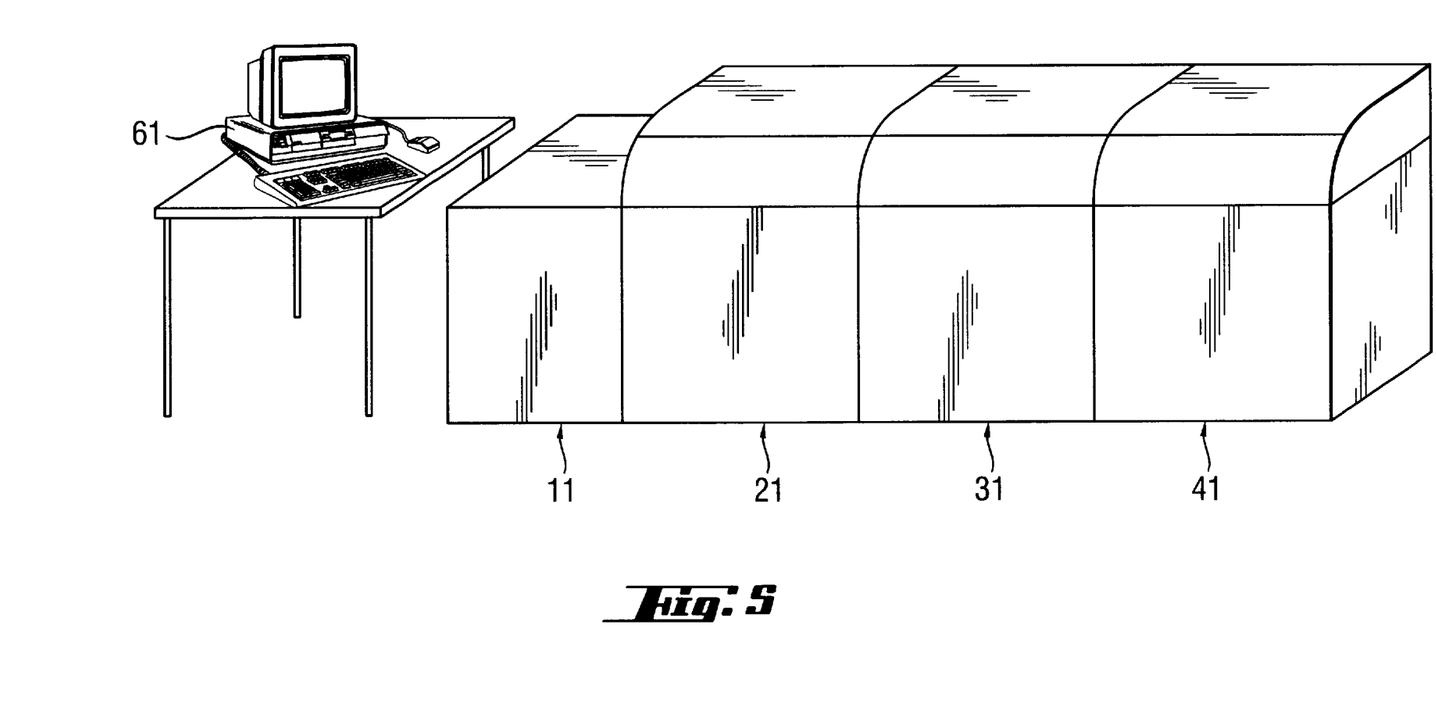
FIG. 5 shows a schematic perspective view of a third embodiment of an analyzer system according to the invention.

FIG. 5 shows a schematic perspective view of a third embodiment of an analyzer system according to the invention. This third embodiment of an analyzer system according to the invention has basically the same structure as the second embodiment shown by FIGS. 3 and 4, but differs therefrom in that it comprises an additional analyzer unit 41.

FIG. 5 shows a central data processing and control unit 61 which provides an overall control at the system level and cooperates with the local control system of each of analyzer units 21, 31, 41.

In a preferred embodiment the alignment of rack supply unit 11 with analyzer units 21, 31 and 41 shown by FIG. 5 is ensured by suitable means, like e.g. positioning pins or equivalent means.

Since the structure and operation of this third embodiment analogous to the structure and operation of the second embodiment it is not described in more detail.

Transfer Line 51

Figure 6:
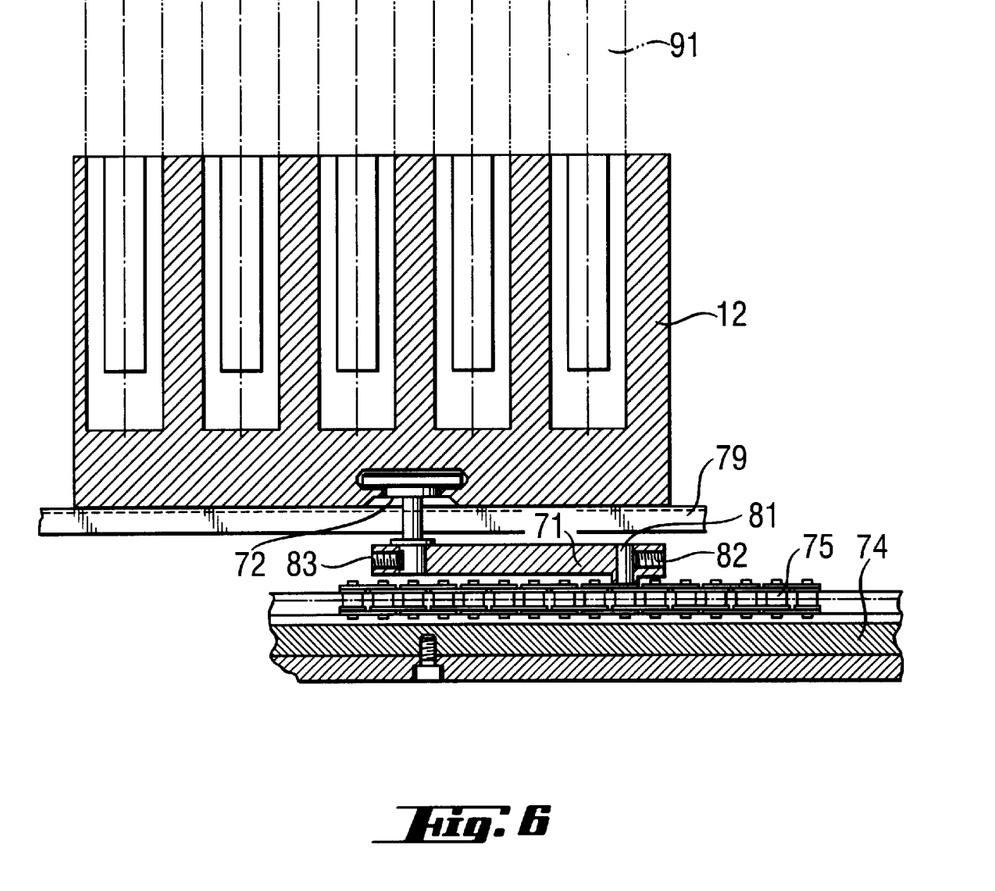
FIG. 6 shows a schematic cross-sectional view of mechanical means for moving a sample rack 12 along transfer line 51 in any of the embodiments according to FIGS. 1 to 5.
Figure 7:
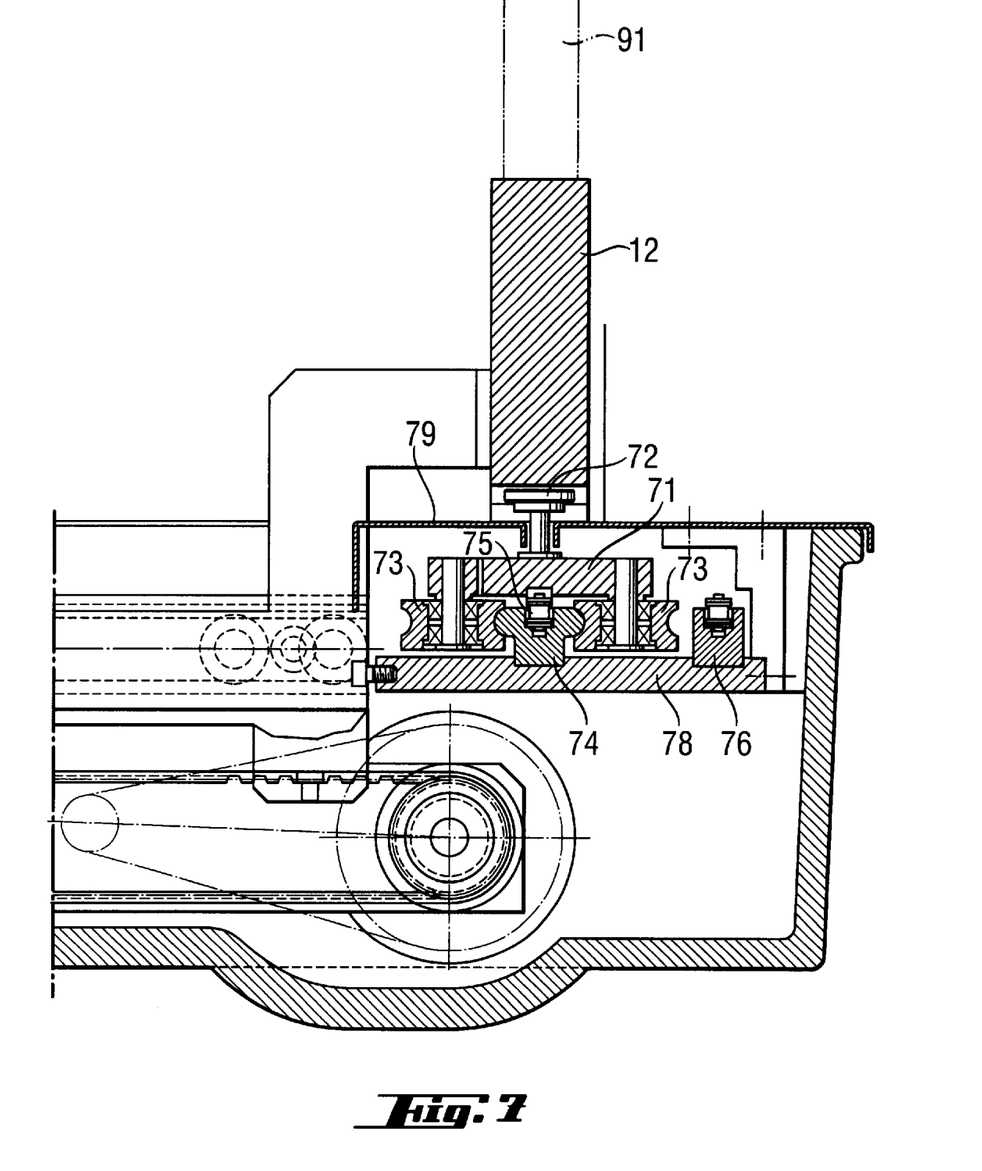
FIG. 7 shows a schematic cross-sectional view of the mechanical means shown in FIG. 6 in a plane perpendicular to the plane of the cross-section represented in FIG. 6.

FIGS. 6 and 7 show schematic cross-sectional views of mechanical components which form part of transfer line 51 and which cooperate with each other for moving a sample rack 12 along transfer line 51 in any of the embodiments according to FIGS. 1 to 5.

As shown by FIGS. 6 and 7 a sample rack 12 is adapted for displaced on a support plate 79. Transport of sample rack 12 in a desired direction is achieved by means of a carriage 71 and a transport chain 75. Carriage 71 is removably connected to sample rack 12 by means of a pin 72. The upper part of a pin 72 of carriage 71 is removably lodged in a corresponding cavity of the bottom wall of sample rack 12.

Guiding rolls 73 and a guiding rail 74 guide movement of carriage 71. A chain guide 76 guides movement of chain 75. A base plate 78 supports guiding rail 74 and mechanical components which cooperate with it.

A carrier bolt 81 connects carriage 71 to chain 75. Pin 72 is fixed to carriage 71 by means of a set screw 83. Carrier bolt 81 is fixed to carriage 71 by means of a set screw 82.

COMMON FEATURES OF THE ABOVE DESCRIBED EMBODIMENTS

For any number of analyzer units the system according to the invention may comprise, central data processing and control unit 61 (shown by FIG. 5) provides an optimized operation of the system components which participate to the transport of the sample racks 12 within a predetermined range of number of samples processed by the system by time unit.

Every sample rack 12 processed by a system according to the invention preferably contains only containers 91 which exclusively contain samples to be analyzed in one or more of the analyzer units which form part of the system.

In preferred embodiments at least one of the analyzer units which form part of the system comprises a working area apt to receive at least one sample rack 26 or 36 which is not brought to the analyzer unit 21 or 31 by means of single transfer line 51, but which is e.g. manually positioned on that working area.

What is claimed is:

1. An automatic analyzer system comprising:
   (a) a rack supply unit capable of containing sample racks comprising containers, wherein each container contains a sample, said rack supply unit comprising:
      (a.1) a rack input device for introducing sample racks into the rack supply unit,
      (a.2) a rack output device for removing sample racks from the rack supply unit,
      (a.3) a buffer unit for storing unprocessed racks before they are transferred from said rack supply unit to a position for examining samples within said containers of said sample racks and for storing sample racks that contain samples that have been examined, and have a probability of being reexamined, and
      (a.4) means for moving an individual sample rack from said rack input device and from said rack output device to said buffer unit and vice versa;
   (b) at least one analyzer unit comprising a local control system, wherein said at least one analyzer unit is for examining a sample sampled from said sample container contained in said individual sample rack wherein said buffer unit is interposed between said rack input/output devices and said at least one analyzer unit,
   (c) a single transfer line for moving said individual sample rack from said buffer unit to said position for examining samples, wherein said position corresponds corresponding to said at least one analyzer unit, and for moving said individual sample rack from said position back to said buffer unit
   (d) means for moving said individual sample rack in opposite senses along said single transfer line and
   (e) means for directing said individual sample rack from said rack input device and said rack output device to said buffer unit and vice versa, and
   (f) means for directing said individual sample rack from said buffer unit to said at least one analyzer unit and vice versa.

2. The automatic analyzer system according to claim 1, wherein said single transfer line comprises at least two separate transfer line portions assembled together.

3. The automatic analyzer system according to claim 2, wherein said at least one analyzer unit comprises one of said at least two transfer line portions.

4. The automatic analyzer system according to claim 1, wherein said at least one analyzer unit comprises plurality of analyzer units each of which is apt to receive said individual sample rack transported by said means for moving said individual sample rack in opposite senses along of said single transfer line.

5. The automatic analyzer system according to claim 4, wherein said single transfer line comprises at least two separate transfer line portions assembled together, and each of said plurality of analyzer units comprises one of said at least two transfer line portions.

6. The automatic analyzer system according to claim 1, wherein said at least one analyzer unit comprises two stationary parking positions, wherein each of said stationary parking positions is apt to receive said individual sample rack.

7. The automatic analyzer system according to claim 6, wherein one of said stationary parking positions is used for receiving said individual sample rack so that said at least one analyzer unit can is enabled to carry out pipetting operations on samples contained within containers of said individual sample rack, whereas the other stationary parking position is used as a stand-by position for another sample rack, wherein both stationary parking positions are apt to be used as either said stand-by position or a position at which pipetting operations are effected on sample containers contained in said another sample rack positioned at the other stationary parking position.

8. The automatic analyzer system according to claim 1, further comprising a central data processing and control unit that provides overall control at the system level and cooperates with the local control system of said at least one analyzer unit.

9. The automatic analyzer system according to claim 8, wherein said central data processing and control unit provides an optimized operation of components of said automatic analyzer system that participate in the transportation of sample racks within a predetermined range of number of samples processed by the system by time unit.

10. The automatic analyzer system according to claim 1, wherein sample racks contain containers that exclusively contain samples to be examined in said at least one analyzer unit.

11. The automatic analyzer system according to claim 1, wherein said at least one analyzer unit comprises a working area apt to receive at least one sample rack that is not brought to said at least one analyzer unit by means of said transfer line.

12. The automatic analyzer system according to claim 1, wherein examining and reexamining said sample at said at least one analyzer unit comprises testing and re-testing an analysis item of said sample with said sample container of said individual sample rack.

* * * * *